United States Patent
Bradshaw et al.

(10) Patent No.: US 9,676,924 B2
(45) Date of Patent: Jun. 13, 2017

(54) TRIESTERS FROM ALPHA-AND-BETA-HYDROXYESTERS

(71) Applicant: Polymer Additives Inc., Independence, OH (US)

(72) Inventors: John D. Bradshaw, Solon, OH (US); Hongqiao Wu, Broadview Heights, OH (US); George F. Schaefer, Strongsville, OH (US); Larry J. Baldwin, Strongsville, OH (US); Ronald J. Raleigh, Jr., Mentor, OH (US); Anne M. Lawson, Akron, OH (US); Brenda Hollo, Broadview Heights, OH (US)

(73) Assignee: Polymer Additives Inc., Independence, OH (US)

( * ) Notice: Subject to any disclaimer, the term of this patent is extended or adjusted under 35 U.S.C. 154(b) by 0 days.

(21) Appl. No.: 14/952,383

(22) Filed: Nov. 25, 2015

(65) Prior Publication Data
US 2016/0145189 A1   May 26, 2016

Related U.S. Application Data

(60) Provisional application No. 62/084,600, filed on Nov. 26, 2014.

(51) Int. Cl.
| | | |
|---|---|---|
| *C07C 69/00* | (2006.01) |
| *C08K 5/12* | (2006.01) |
| *C07C 67/08* | (2006.01) |
| *C07C 67/11* | (2006.01) |
| *C07C 69/75* | (2006.01) |

(52) U.S. Cl.
CPC ................ *C08K 5/12* (2013.01); *C07C 67/08* (2013.01); *C07C 67/11* (2013.01); *C07C 69/75* (2013.01); *C07C 2101/14* (2013.01)

(58) Field of Classification Search
CPC ......... C07C 69/75; C07C 67/08; C07C 67/11; C07C 2101/14; C07C 67/10; C07C 69/753; C08K 5/12
See application file for complete search history.

(56) References Cited

U.S. PATENT DOCUMENTS

| | | |
|---|---|---|
| 2,072,739 A | 3/1937 | Dykstra et al. |
| 2,073,937 A | 3/1937 | Kyrides |
| 2,073,938 A | 3/1937 | Kyrides |
| 2,120,755 A | 6/1938 | Kyrides |
| 2,120,756 A | 6/1938 | Kyrides |
| 2,184,426 A | 12/1939 | Kocher et al. |
| 2,260,295 A | 10/1941 | Carruthers et al. |
| 2,526,554 A | 10/1950 | Gresham et al. |
| 2,561,315 A | 7/1951 | Richard |
| 2,608,577 A | 8/1952 | Weesner |
| 2,712,025 A | 6/1955 | Rehberg et al. |
| 3,155,714 A | 11/1964 | Mills |
| 3,175,989 A | 3/1965 | Cannon et al. |
| 3,538,145 A | 11/1970 | Hirzy |
| 4,421,885 A | 12/1983 | Tsuda et al. |
| 4,620,026 A | 10/1986 | Siegel |
| 5,107,016 A | 4/1992 | Pennetreau |
| 8,377,151 B2 | 2/2013 | McMurry et al. |
| 2015/0038734 A1 | 2/2015 | Weakley et al. |

FOREIGN PATENT DOCUMENTS

| | | |
|---|---|---|
| WO | WO2012/158250 | 11/2012 |
| WO | WO2014/014337 | 1/2014 |

OTHER PUBLICATIONS

Organic Syntheses: Working with Hazardous Chemicals.
Allen Padwa: PHA Modifiers as Polymeric Plasticizes and Process Aids; Indianapolis 2014.
Linglin Wu, Saikat Dutta, and Mark Mascal: Efficient, Chemical-Catalytic Approach to the Production of 3-Hydroxypropanoic Acid by Oxidation of Biomass-Derived Levulinic Acid With Hydrogen Peroxide; ChemSusChem 2015, 8, 1167-1169.

*Primary Examiner* — Yevegeny Valenrod
*Assistant Examiner* — Blaine G Doletski
(74) *Attorney, Agent, or Firm* — Medley, Behrens & Lewis, LLC

(57) ABSTRACT

A method of making a benzyl cis-cyclohexane 1,2-dicarboxylate triester having the steps: a. forming a reaction mixture by reacting the following three components: i. a synthetic or biobased reagent selected from the group consisting of an alpha-hydroxyester and a beta-hydroxyester, ii. an anhydride selected from the group consisting of cis-hexahydrophthalic anhydride, 4-methylcyclohexane-1,2-dicarboxylic anhydride, and 3-methylcyclohexane-1,2-dicarboxylic anhydride, and iii. an alkylamine catalyst; and b. contacting benzyl chloride with the reaction mixture to yield a product that is free of phthalates and includes at least one benzyl cis-cyclohexane 1,2-dicarboxylate triester.

17 Claims, 5 Drawing Sheets

TRIESTERS FROM ALPHA-AND-BETA-HYDROXYESTERS

CROSS-REFERENCE TO RELATED APPLICATIONS

This application claims priority to U.S. provisional patent application 62/084,600 filed on Nov. 26, 2014. All of the subject matter of U.S. provisional patent application 62/084,600 is hereby incorporated by reference into this application.

BACKGROUND OF THE INVENTION

(1) Field of Invention

Synthesis of benzyl cis-cyclohexane-1,2-dicarboxylate triesters from α- and β-hydroxyesters is effected by the reaction of at least one hydroxyester, an anhydride and a benzyl group donating compound.

(2) Description of Related Art

Plasticizers are compounds or mixtures of compounds that are added to polymer resins to impart softness and flexibility. Phthalic acid diesters, also called phthalates, are the primary plasticizers for most flexible polymer products, especially polymer products formed from polyvinyl chloride (PVC) and other vinyl polymers. Examples of common phthalate plasticizers include: diisononyl phthalate (DINP), benzyl butyl phthalate (BBP), and di-2-ethylhexyl-phthalate (DEHP).

It would be useful in the plastics and plasticizers industries to provide plasticizers that are phthalate-free and biobased to thereby reduce the carbon footprint of industrial processes.

BRIEF SUMMARY OF THE INVENTION

A method of making a benzyl cis-cyclohexane 1,2-dicarboxylate triester having the steps: a. forming a reaction mixture by reacting the following three components: i. a synthetic or biobased reagent selected from the group consisting of an alpha-hydroxyester and a beta-hydroxyester, ii. an anhydride selected from the group consisting of cis-hexahydrophthalic anhydride, 4-methylcyclohexane-1,2-dicarboxylic anhydride, and 3-methylcyclohexane-1,2-dicarboxylic anhydride, and iii. an alkylamine catalyst; and b. contacting benzyl chloride with the reaction mixture to yield a product that is free of phthalates and includes at least one benzyl cis-cyclohexane 1,2-dicarboxylate triester.

A method of making a dibenzyl cis-cyclohexane-1,2-dicarboxylate having the steps: a. forming a reaction mixture by reacting the following three components: i. a cis-hexahydrophthalic anhydride, ii. an alcohol, and iii. an alkylamine catalyst; and b. adding benzyl chloride to the reaction mixture to form at least one dibenzyl cis-cyclohexane-1,2-dicarboxylate.

A method of making a benzyl 2-[(alkoxycarbonylmethylthio)carbonyl]cyclohexanecarboxylate having the steps: a. forming a reaction mixture by reacting the following three components: i. a thioglycolic acid ester, ii. a cis-hexahydrophthalic anhydride, and iii. an alkylamine catalyst; and b. adding benzyl chloride to the reaction mixture to form at least one benzyl 2-[(alkoxycarbonylmethylthio)carbonyl] cyclohexanecarboxylate.

A method of making a dibenzyl cis-cyclohexane-1,2-dicarboxylate having the steps: a. forming a reaction mixture by reacting the following three components: i. a cis-hexahydrophthalic anhydride, ii. water, and iii. an alkylamine catalyst; and b. adding benzyl chloride to the reaction mixture to form at least one dibenzyl cis-cyclohexane-1,2-dicarboxylate.

A composition having a benzyl cis-cyclohexane-1,2-dicarboxylate triester having the structure:

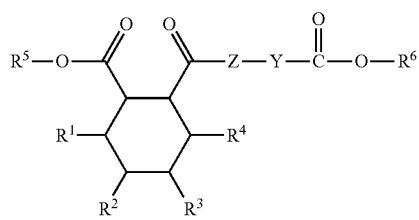

wherein R1 and R4 are independently selected from the group consisting of H, CH3, bridging O, bridging CH2, and bridging CH2-CH2, with each bridging unit defining coincident R1 and R4 groups; wherein R2 and R3 are independently selected from the group consisting of H, CH3, and C1-C30 linear or branched, cyclic or acyclic, substituted or unsubstituted hydrocarbyl groups; wherein R5 is selected from the group consisting of benzyl and substituted benzyl groups; wherein R6 is a C1-C12 linear or branched, substituted or unsubstituted, aryl or aliphatic hydrocarbyl group; wherein Z is O or S; wherein Y is selected from the group consisting of CH2, CH(R7), C(CH3)2, CH2-CH2, CH(R7)-CH2, and CH2-C(=CH2); and wherein R7 is selected from the group consisting of H and a C1-C12 linear or branched, substituted or unsubstituted, aryl or aliphatic hydrocarbyl group.

Benzyl cis-cyclohexane-1,2-dicarboxylates useful as plasticizers are synthesized from a dicarboxylic acid anhydride, synthetic or biobased hydroxyesters and benzyl chloride. Alternatively the same plasticizers are synthesized from a dicarboxylic acid anhydride, benzyl alcohol and chloro-esters. Plastisols including the benzyl cis-cyclohexane-1,2-dicarboxylates of the invention are also envisioned.

An embodiment of the invention is a method of making a benzyl cis-cyclohexane-1,2-dicarboxylate comprising: (a) providing and reacting the following to form a reaction mixture: (i) a synthetic or biobased reagent selected from the group consisting of an alpha-hydroxyester, and a beta-hydroxyester, (ii) an anhydride selected from the group consisting of cis-hexahydrophthalic anhydride, 4-methylcyclohexane-1,2-dicarboxylic anhydride, 3-methylcyclohexane-1,2-dicarboxylic anhydride, and (iii) an alkylamine catalyst, and (b) contacting benzyl chloride with the reaction mixture to form a product that is free of phthalates and includes at least one benzyl cis-cyclohexane-1,2-dicarboxylate triester from an α- or β-hydroxyester.

An embodiment of the invention is a method of plasticizing a plastic composition comprising combining: (a) any benzyl cis-cyclohexane-1,2-dicarboxylate disclosed herein or made by any method herein with (b) a plastic composition.

An embodiment of the invention is a method of making a dibenzyl cis-cyclohexane-1,2-dicarboxylate comprising: (a) providing and reacting the following to form a reaction mixture: (i) a cis-hexahydrophthalic anhydride, (b) an alcohol (c) an alkyl amine catalyst, and (b) adding benzyl chloride to the reaction mixture to form a dibenzyl cis-cyclohexane-1,2-dicarboxylate.

An embodiment of the invention is a method of making a thioglycolic acid ester cyclohexane-1,2-dicarboxylate comprising: (a) providing and reacting the following to form a reaction mixture: (i) a thioglycolic acid ester, (ii) a cis-hexahydrophthalic anhydride, and (iii) an alkyl amine catalyst, and (b) adding benzyl chloride to the reaction mixture to form at least one benzyl cis-cyclohexane-1,2-dicarboxylate diester-thioester from a thioglycolic acid ester.

Embodiments of the invention are plastisols including at least one of the following: benzyl(methyl 2-carboxyethyl) cyclohexane-1,2-dicarboxylate; benzyl(ethyl 2-carboxyethyl)cyclohexane-1,2-dicarboxylate; benzyl(propyl 2-carboxyethyl)cyclohexane-1,2-dicarboxylate; benzyl(butyl 2-carboxyethyl)cyclohexane-1,2-dicarboxylate; benzyl(2-ethylhexyl 2-carboxyethyl)cyclohexane; benzyl(methyl 2-carboxyethyl)4-methylcyclohexane-1,2-dicarboxylate; benzyl(ethyl 2-carboxyethyl) 4-methylcyclohexane-1,2-dicarboxylate; benzyl(propyl 2-carboxyethyl) 4-methylcyclohexane-1,2-dicarboxylate; benzyl(butyl 2-carboxyethyl) 4-methylcyclohexane-1,2-dicarboxylate; benzyl(2-ethylhexyl 2-carboxyethyl) 4-methylcyclohexane; benzyl(methyl lactyl)cyclohexane-1,2-dicarboxylate; benzyl(ethyl lactyl) cyclohexane-1,2-dicarboxylate; benzyl(propyl lactyl)cyclohexane-1,2-dicarboxylate; benzyl(butyl lactyl)cyclohexane-1,2-dicarboxylate; benzyl(2-ethylhexyl lactyl)cyclohexane-1,2-dicarboxylate; benzyl(methyl carboxymethyl) cyclohexane-1,2-dicarboxylate; benzyl(ethyl carboxymethyl)cyclohexane-1,2-dicarboxylate; benzyl(propyl carboxymethyl)cyclohexane-1,2-dicarboxylate; benzyl (butyl carboxymethyl)cyclohexane-1,2-dicarboxylate; benzyl(2-ethylhexyl carboxymethyl)cyclohexane-1,2-dicarboxylate; and benzyl(butyl mandelyl)cyclohexane-1,2-dicarboxylate.

An embodiment of the invention is a plastisol including benzyl(methyl 2-carboxyethyl)cyclohexane-1,2-dicarboxylate. An embodiment of the invention is a plastisol including benzyl(ethyl 2-carboxyethyl)cyclohexane-1,2-dicarboxylate. An embodiment of the invention is a plastisol including benzyl(propyl 2-carboxyethyl)cyclohexane-1,2-dicarboxylate.

An embodiment of the invention is a plastisol including benzyl(butyl 2-carboxyethyl)cyclohexane-1,2-dicarboxylate. An embodiment of the invention is a plastisol including benzyl(2-ethylhexyl 2-carboxyethyl)cyclohexane-1,2-dicarboxylate. An embodiment of the invention is a plastisol including benzyl(methyl 2-carboxyethyl) 4-methylcyclohexane-1,2-dicarboxylate. An embodiment of the invention is a plastisol including benzyl(ethyl 2-carboxyethyl) 4-methylcyclohexane-1,2-dicarboxylate. An embodiment of the invention is a plastisol including benzyl(propyl 2-carboxyethyl) 4-methylcyclohexane-1,2-dicarboxylate. An embodiment of the invention is a plastisol including benzyl(butyl 2-carboxyethyl) 4-methylcyclohexane-1,2-dicarboxylate. An embodiment of the invention is a plastisol including benzyl(2-ethylhexyl 2-carboxyethyl) 4-methylcyclohexane-1,2-dicarboxylate. An embodiment of the invention is a plastisol including benzyl(methyl lactyl)cyclohexane-1,2-dicarboxylate. An embodiment of the invention is a plastisol including benzyl(ethyl lactyl)cyclohexane-1,2-dicarboxylate. An embodiment of the invention is a plastisol including benzyl(propyl lactyl)cyclohexane-1,2-dicarboxylate. An embodiment of the invention is a plastisol including benzyl (butyl lactyl)cyclohexane-1,2-dicarboxylate; An embodiment of the invention is a plastisol including benzyl(2-ethylhexyl lactyl)cyclohexane-1,2-dicarboxylate. An embodiment of the invention is a plastisol including benzyl (methyl carboxymethyl)cyclohexane-1,2-dicarboxylate. An embodiment of the invention is a plastisol including benzyl (ethyl carboxymethyl)cyclohexane-1,2-dicarboxylate. An embodiment of the invention is a plastisol including benzyl (propyl carboxymethyl)cyclohexane-1,2-dicarboxylate. An embodiment of the invention is a plastisol including benzyl (butyl carboxymethyl)cyclohexane-1,2-dicarboxylate. An embodiment of the invention is a plastisol including benzyl (2-ethylhexyl carboxymethyl)cyclohexane-1,2-dicarboxylate. An embodiment of the invention is a plastisol including benzyl(butyl mandelyl)cyclohexane-1,2-dicarboxylate.

An embodiment of the invention is a method of plasticizing a thermoplastic polymer comprising contacting the thermoplastic polymer with benzyl(methyl 2-carboxyethyl) cyclohexane-1,2-dicarboxylate. An embodiment of the invention is a method of plasticizing a thermoplastic polymer comprising contacting the thermoplastic polymer with benzyl(ethyl 2-carboxyethyl)cyclohexane-1,2-dicarboxylate. An embodiment of the invention is a method of plasticizing a thermoplastic polymer comprising contacting the thermoplastic polymer with benzyl(propyl 2-carboxyethyl)cyclohexane-1,2-dicarboxylate. An embodiment of the invention is a method of plasticizing a thermoplastic polymer comprising contacting the thermoplastic polymer with benzyl(butyl 2-carboxyethyl)cyclohexane-1,2-dicarboxylate. An embodiment of the invention is a method of plasticizing a thermoplastic polymer comprising contacting the thermoplastic polymer with benzyl(2-ethylhexyl 2-carboxyethyl)cyclohexane-1,2-dicarboxylate. An embodiment of the invention is a method of plasticizing a thermoplastic polymer comprising contacting the thermoplastic polymer with benzyl(methyl 2-carboxyethyl) 4-methylcyclohexane-1,2-dicarboxylate. An embodiment of the invention is a method of plasticizing a thermoplastic polymer comprising contacting the thermoplastic polymer with benzyl(ethyl 2-carboxyethyl) 4-methylcyclohexane-1,2-dicarboxylate. An embodiment of the invention is a method of plasticizing a thermoplastic polymer comprising contacting the thermoplastic polymer with benzyl(propyl 2-carboxyethyl) 4-methylcyclohexane-1,2-dicarboxylate. An embodiment of the invention is a method of plasticizing a thermoplastic polymer comprising contacting the thermoplastic polymer with benzyl(butyl 2-carboxyethyl) 4-methylcyclohexane-1,2-dicarboxylate. An embodiment of the invention is a method of plasticizing a thermoplastic polymer comprising contacting the thermoplastic polymer with benzyl(2-ethylhexyl 2-carboxyethyl) 4-methylcyclohexane-1,2-dicarboxylate. An embodiment of the invention is a method of plasticizing a thermoplastic polymer comprising contacting the thermoplastic polymer with benzyl(methyl lactyl)cyclohexane-1,2-dicarboxylate. An embodiment of the invention is a method of plasticizing a thermoplastic polymer comprising contacting the thermoplastic polymer with benzyl(ethyl lactyl) cyclohexane-1,2-dicarboxylate. An embodiment of the invention is a method of plasticizing a thermoplastic polymer comprising contacting the thermoplastic polymer with benzyl(propyl lactyl)cyclohexane-1,2-dicarboxylate. An embodiment of the invention is a method of plasticizing a thermoplastic polymer comprising contacting the thermoplastic polymer with benzyl(butyl lactyl)cyclohexane-1,2-dicarboxylate; An embodiment of the invention is a method of plasticizing a thermoplastic polymer comprising contacting the thermoplastic polymer with benzyl(2-ethylhexyl lactyl)cyclohexane-1,2-dicarboxylate. An embodiment of the invention is a method of plasticizing a thermoplastic polymer comprising contacting the thermoplastic polymer with benzyl(methyl carboxymethyl)cyclohexane-1,2-dicarboxylate. An embodiment of the invention is a method of plasticizing a thermoplastic polymer comprising contacting the thermoplastic polymer with benzyl(ethyl carboxymethyl)cyclohexane-1,2-dicarboxylate. An embodiment of the invention is a method of plasticizing a thermoplastic polymer comprising contacting the thermoplastic polymer with benzyl(propyl carboxymethyl)cyclohexane-1,2-dicarboxylate. An embodiment of the invention is a method of plasticizing a thermoplastic polymer comprising contacting the thermoplastic polymer with benzyl(butyl carboxymethyl)cyclohexane-1,2-dicarboxylate. An embodiment of the invention is a method of plasticizing a thermoplastic polymer comprising contacting the thermoplastic polymer with benzyl(2-ethylhexyl carboxymethyl)cyclohexane-1,2-dicarboxylate. An embodiment of the invention is a method of plasticizing a thermoplastic polymer comprising contacting the thermoplastic polymer with benzyl(butyl mandelyl)cyclohexane-1,2-dicarboxylate.

DETAILED DESCRIPTION OF THE INVENTION

Figure 1:
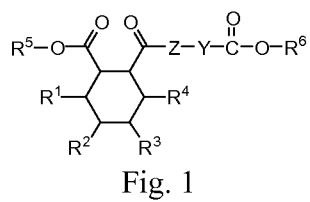
FIG. 1 shows an embodiment's generic chemical structure and defined groups.

The compounds of the invention are used as plasticizers in thermoplastic resins, particularly halogenated thermoplastic resins, such as vinyl halide resin compositions. FIG. 1 shows a proposed generic structure for triesters derived from α- and β-hydroxyesters of this invention. In the generic structure of FIG. 1, the various groups are defined as follows:

$R^1$ and $R^4$ are independently —H, —$CH_3$, bridging —O—, bridging —$CH_2$— or bridging —$CH_2$—$CH_2$— (each bridging unit defining coincident $R^1$ and $R^4$ groups), $R^2$ and $R^3$ are independently —H, —$CH_3$, or other C1-C30 linear or branched, cyclic or acyclic, substituted or unsubstituted hydrocarbyl groups [See for example D. Batzel and F. X. Woolard (Amryis Biotechnologies) WO2012/158250 A1.], $R^5$ is selected from benzyl, or substituted benzyl groups, $R^6$ is a C1-C12 linear or branched, substituted or unsubstituted, aryl or aliphatic hydrocarbyl group, Z is —O— or —S—, and Y is selected from the following groups:
(α) —$CH_2$—, —$CH(R^7)$—, or —$C(CH_3)_2$—
(β) —$CH_2$—$CH_2$—, —$CH(R^7)$—$CH_2$—, or —$CH_2$—C(=$CH_2$)—, and Within the Y group, $R^7$ is —H, or a C1-C12 linear or branched, substituted or unsubstituted, aryl or aliphatic hydrocarbyl group.

In the generic formula of FIG. 1, in cases where $R^5$ is not equivalent to $R^6$, it is advantageous for the outlying ester to be formed prior to reaction with the anhydride. Such preformed esters are available as α- and β-hydroxyesters and analogous thiolesters as defined by the Y and Z selections above. It is advantageous to limit the amount of the preformed α- and β-hydroxyesters and analogous thiolesters. This is especially true in the cases where Z is —S— because if an excess of thiol was used, the residual thiol would have an unpleasant odor. Further an excess of α- and β-hydroxyesters and analogous thiolesters could cause separation issues in purification of the final product.

Examples of the α-groups above include methyl 2-hydroxyisobutyrate, ethyl 2-hydroxyisobutyrate, and tert-butyl 2-hydroxyisobutyrate. An example of the β-groups above include ethyl 2-(hydroxymethyl)acrylate.

Figure 2:
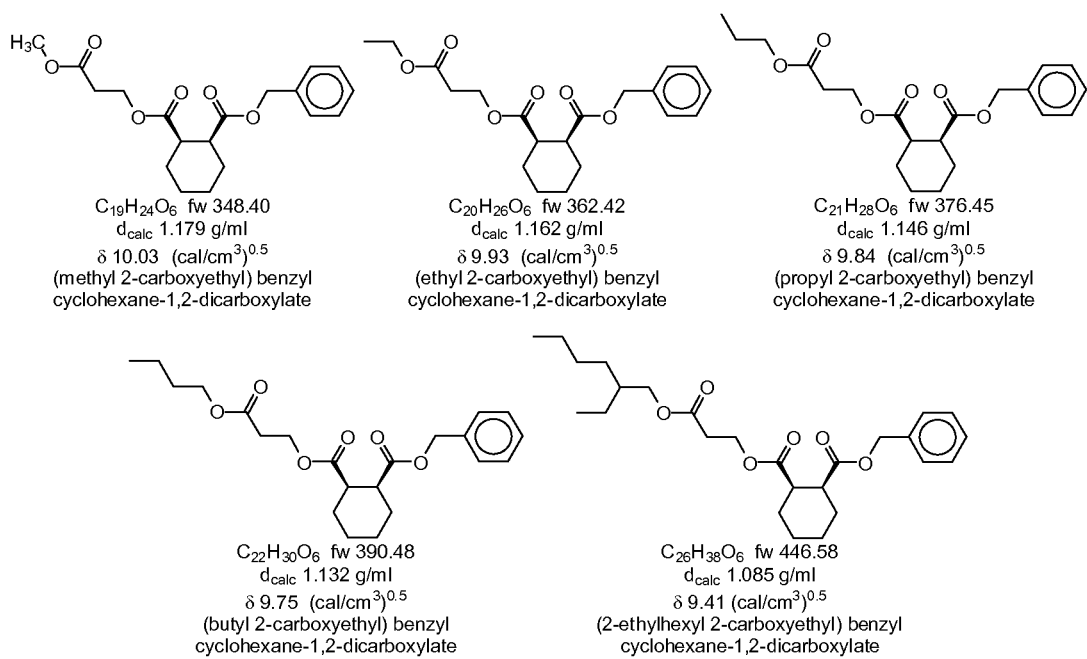
FIG. 2 shows benzyl cis-cyclohexane-1,2-dicarboxylate triesters from selected beta-hydroxy esters with calculated densities and solubility parameters ($\delta$).
Figure 3:
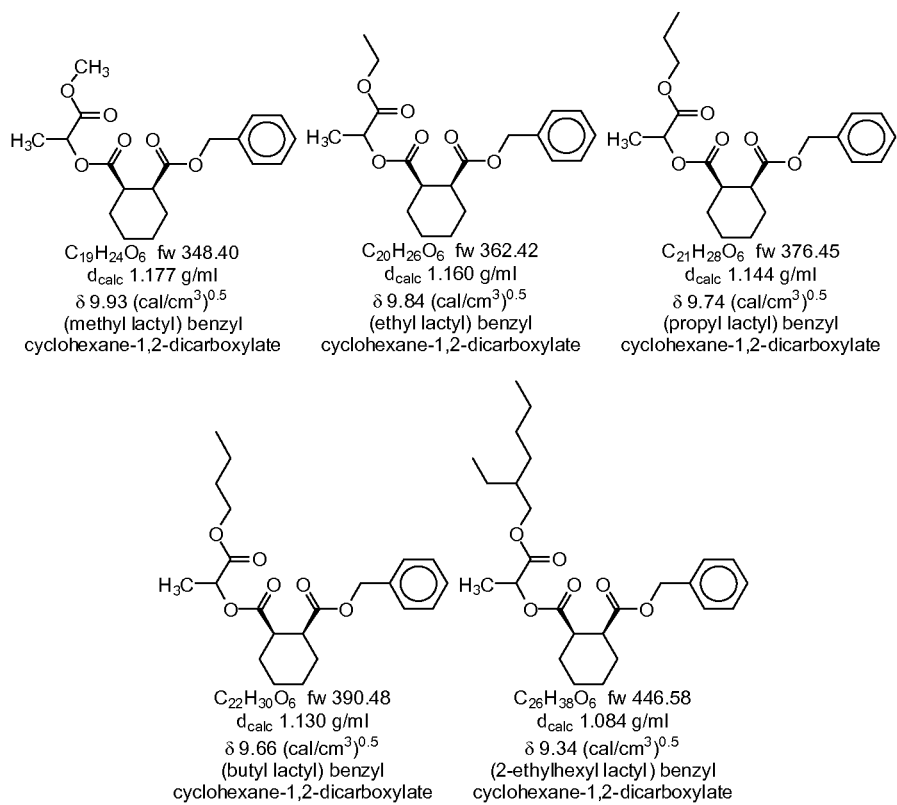
FIG. 3 shows alkyl-lactyl benzyl cis-cyclohexane-1,2-dicarboxylates with calculated densities and solubility parameters ($\delta$).
Figure 4:
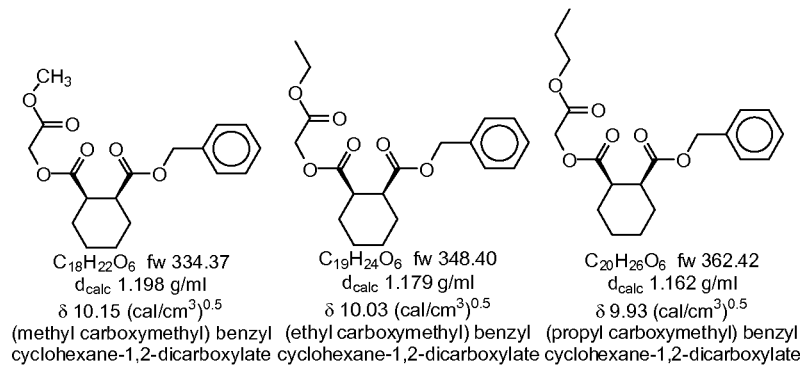
FIG. 4 shows alkyl-glycolyl benzyl cis-cyclohexane-1,2-dicarboxylates with calculated densities and solubility parameters ($\delta$).
Figure 5:
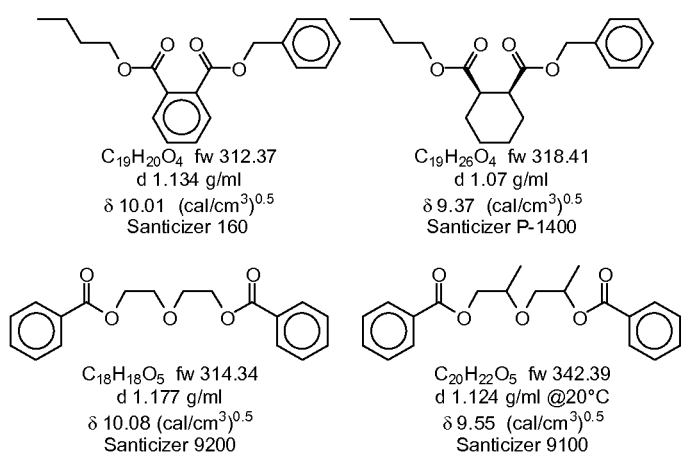
FIG. 5 shows established fast-fusing plasticizers with densities and solubility parameters ($\delta$).

According to Sears and Darby [*The Technology of Plasticizers*], PVC has a Small's solubility parameter of 9.66 $(cal/cm^3)^{0.5}$. Compounds depicted in FIG. 2 through FIG. 4 have predicted solubility parameters similar to PVC and might prove superior to known fast fusing plasticizers (See FIG. 5.), at least in their affinity for PVC and derived permanence in plastisols. Selected family members have solubility parameters ($\delta$) spanning the range of 9.34 to 10.15 $(cal/cm^3)^{0.5}$, encompassing that of PVC.

Figure 6:
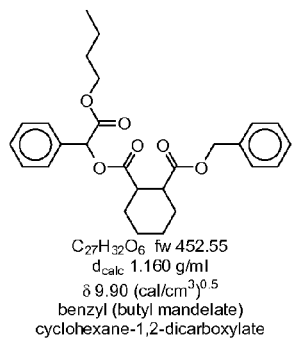
FIG. 6 shows benzyl(butyl mandelyl)cyclohexane-1,2-dicarboxylate.

Esters of mandelic acid are alpha-hydroxy esters and would be useful starting materials in making benzyl(alkyl mandelyl)cyclohexane-1,2-dicarboxylates. An example of such a compound derived from butyl mandelate or butt 2-hydroxy-2-phenylacetate [CAS No. 14007-02-4] is depicted in FIG. 6. Similar phenyl substituted alpha-hydroxy esters that are useful are: propyl 2-hydroxy-2-phenylacetate [CAS No. 7249-07-2], butan-2-yl 2-hydroxy-2-phenylacetate [CAS No. 6290-32-0], propyl 2-hydroxy-2-(4-methyl phenyl)acetate [CAS No. 15913-17-4], and butyl 2-hydroxy-2-(4-methyl phenyl)acetate [CAS No. 6641-81-2].

Many other benefits will no doubt become apparent from future application and development of this technology. All patents, published applications, and articles noted herein are hereby incorporated by reference in their entirety.

Figure 7:
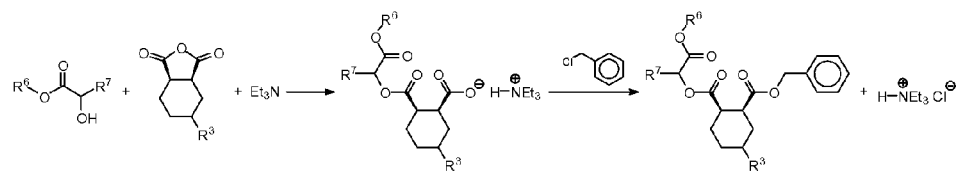
FIG. 7 shows a synthesis scheme for alkyl glycolyl ($R^7$=H) and alkyl lactyl ($R^7$=Me) benzyl cis-cyclohexane-1,2-dicarboxylates.
Figure 8:
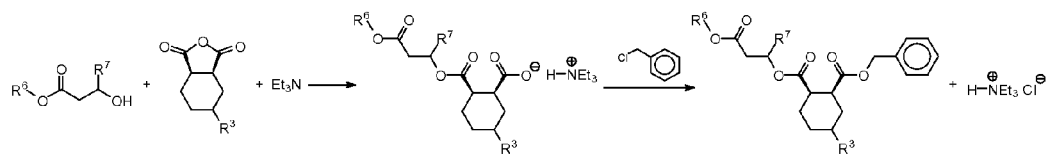
FIG. 8 shows a synthesis scheme for (alkyl carboxyethyl) benzyl cis-cyclohexane-1,2-dicarboxylates.

Alkyl lactyl, alkyl glycolyl, and alkyl carboxyethyl benzyl cis-cyclohexane-1,2-dicarboxylic acid triesters can be synthesized by established processes. The process using alpha-hydroxyacid esters is depicted in FIG. 7, and the process using beta-hydroxyacid esters is depicted in FIG. 8. The predominantly cis-configuration of the starting hexahydrophthalic anhydride (HHPA) dictates the stereo chemistry of two vicinal carbons of the central cyclohexane ring.

Starting alpha-hydroxy esters can be selected from lactate esters that are commercially produced, biobased, nontoxic, biodegradable, and have excellent solvent properties. Ethyl lactate is produced from lignocellulose materials (such as wheat straw, distilled dried grains with solubles, and brewers' grains) or lactose whey. Archer Daniels Midland (ADM) offers Electronic, Food Chemicals Codex, and Solvent grades of ethyl lactate. Vertec Biosolvents offers technical grade ethyl lactate. Several lactate esters ranging from methyl lactate to 2-ethylhexyl lactate are offered by Purac Biochemical, Galactic, and others.

Starting substituted alpha-hydroxy esters can be selected from available glycolic acid esters. Glycolic acid is commercially produced by DuPont. Butyl glycolate is commercially produced by Celanese. Methyl and ethyl glycolates may also be available.

Starting beta-hydroxyesters can be selected from 3-hydroxypropionic acid and 3-hydroxy butyric acid esters. 3-Hydroxypropionic acid (3-HP) can be derived from corn and glycerol. 3HP is the target of biochemical processes championed by two groups: 1. BASF, Cargill, and Novozymes, and 2. Dow Chemical and OPX Biotechnologies. They seek 3-HP en route to bio-derived acrylic acid. Both groups have successfully produced bio-derived 3-HP on pilot scales. 3-HP can be produced in a non-biochemical method from ethylene cyanohydrin. Eastman now offers commercial quantities of Omnia butyl 3-hydroxybutyrate as a cleaning solvent.

Mixtures of the individual compounds and blends of this invention are envisioned arising from use of mixtures of beta-hydroxyesters having different $R^7$ groups. Such mixtures might arise from use of mixtures of beta-hydroxyesters found in bio-based polyhydroxyalkanoates. Alcoholysis of polyhydroxyalkanoates will produce the corresponding alkyl beta-hydroxyesters. [Ref. Jansen Jacob Eden, Thomas L. Gresham (B. F. Goodrich) U.S. Pat. No. 2,526,554, "Preparation of beta-Hydroxy Carboxylic Acid Esters by Alcoholysis of Linear Polyesters Derived from beta-Lactones"; Pascal Pennetreau (Solvay and Cie) U.S. Pat. No. 5,107,016, "Process for the Preparation of β-Hydroxybutyric Acid Esters"; and Zackery Allen McMurry, U.S. Pat. No. 8,377,151, "Starting from Polyhydroxyalkanoates; End Products Include Specialty Chemicals Crotonic Acid Ethyl Ester, Ethyl 3-Hydroxybutyrate, and Ethyl 3-Ethoxybutyrate"] Examples include the following combinations of $R^7$ groups: —$CH_3$ and —$CH_2$—$CH_3$, —$CH_3$ and —$(CH_2)_2$—$CH_3$, —$CH_3$ and —$(CH_2)_4$—$CH_3$, —$CH_3$ and —$(CH_2)_6$—$CH_3$, etc. When beta-hydroxyesters are derived in part by biological processes, enantiomeric excesses of the R-configuration are observed of the chiral center having the $R^7$ substituent. Compounds of this invention derived using methods disclosed herein from such chiral beta-hydroxyesters will retain this chiral center configuration. Meredian, Metabolix with Archer Daniels Midland, TainAn Biologic Material, and Tianjin Green Bio-Science are examples of companies that produce polyhydroxyalkanoates via fermentation with such compositions.

Figure 9:
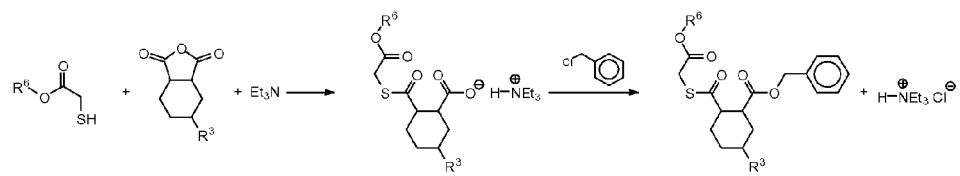
FIG. 9 shows a synthesis scheme for derivatives of thioglycolic acid esters.

The product of a thioglycolic acid ester, cyclohexane-1,2-dicarboxylic acid anhydride, in the presence of a tertiary amine further reacted with benzyl chloride is a new compound useful as a plasticizer. The reaction scheme is depicted in FIG. 9. Names for such products might be approximated as: benzyl 2-[(alkoxycarbonylmethylthio)carbonyl]cyclohexanecarboxylate, wherein the alkoxy corresponds with the alkyl thioglycolate. Useful thioglycolic acid esters are: 2-ethylhexyl thioglycolate [CAS No. 7659-86-1], methyl thioglycolate [CAS No. 2365-48-2], isopropyl mercaptoacetate [CAS No. 7383-61-1], butyl thioglycolate [CAS No. 10047-28-6], ethyl 2-mercaptopropionate, isopentyl mercaptoacetate, isooctyl mercaptoacetate, nonyl mercaptoacetate, and dodecyl mercaptoacetate. The starting thiol group needs to be completely reacted to eliminate odor.

The product of a 3-mercaptopropionic acid ester, cyclohexane-1,2-dicarboxylic acid anhydride, in the presence of a tertiary amine further reacted with benzyl chloride are new compounds useful as a plasticizers. The reaction scheme is analogous to that depicted in FIG. 8 for (alkyl carboxyethyl) benzyl cis-cyclohexane-1,2-dicarboxylates. Useful 3-mercaptopropionic acid esters are: methyl 3-mercaptopropionate, isooctyl 3-mercaptopropionate, and dodecyl 3-mercaptopropionate. As with the thioglycolic acid esters, the starting thiol group of the 3-mercaptopropionic acid esters needs to be completely reacted to eliminate odor.

Figure 10:
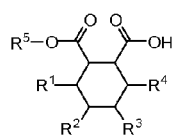
FIG. 10 shows a half ester resulting from diacid contaminant in anhydride.

The starting anhydride typically contains some diacid generated by exposure to moisture. Residual acid, in the form of the structure depicted in FIG. 10, contributes to undesirable acidity, forms soaps that are difficult to separate from the desired product, and does not beneficially contribute to end-use applications.

Figure 11:
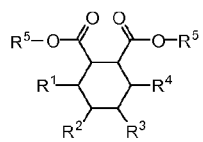
FIG. 11 shows a product of diacid and excess tertiary amine and $R^5$—X reagents.

When limiting the α- and β-hydroxyesters and analogous thioesters, it is desirable to use an excess of the tertiary amine and $R^5$—X reagents. X being a halogen (Cl, Br, or I), triflate, mesylate or other good leaving group. $R^5$ being benzyl or other aryl-containing group. The excess tertiary amine and $R^5$—X reagents will help to consume the diacid forming the diaryl diester product depicted in FIG. 11. The diaryl diester compound is typically of greater density and can aid separation during purification. The diaryl diesters are also good plasticizers in their own right.

Further advantage is found in the use of an excess of tertiary amine and $R^5$—X reagents that will by Le Chatlier's Principle help drive the bimolecular nucleophilic substitution ($S_N2$) reaction leading to the final product, in producing compounds of this invention. This is surprising in that tertiary amine and $R^5$—X reagents typically undergo a competing reaction to form quaternary ammonium salts.

Figure 12:
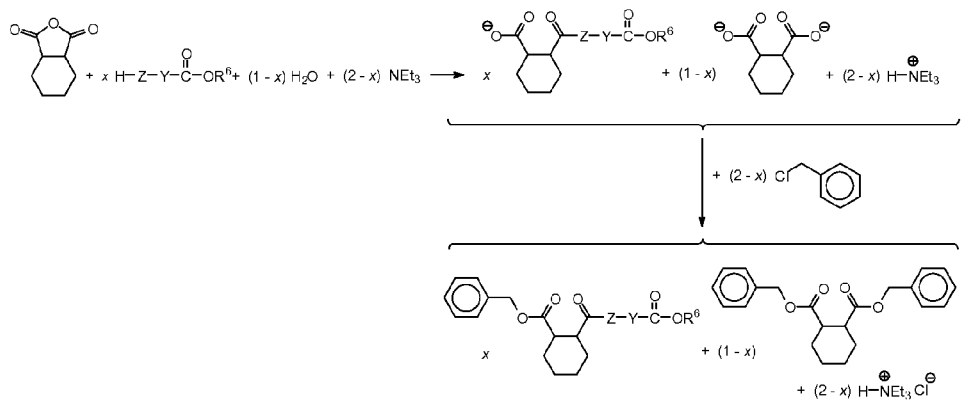
FIG. 12 shows introduction of water results in dibenzyl cyclohexane-1,2-dicarboxylate.

Blends of benzyl cyclohexane-1,2-dicarboxylate triesters with symmetrical dibenzyl cyclohexane-1,2-dicarboxylate will result from opportunistic water or deliberate addition of water to the first reaction with the cyclic carboxylic acid anhydride. The scheme is depicted in FIG. 12. Hence blends might be obtained of dibenzyl cyclohexane-1,2-dicarboxylate with (alkyl glycolyl)benzyl cyclohexane-1,2-dicarboxylates, (alkyl lactyl)benzyl cyclohexane-1,2-dicarboxylates, and (alkyl carboxyethyl)benzyl cyclohexane-1,2-dicarboxylates.

Figure 13:
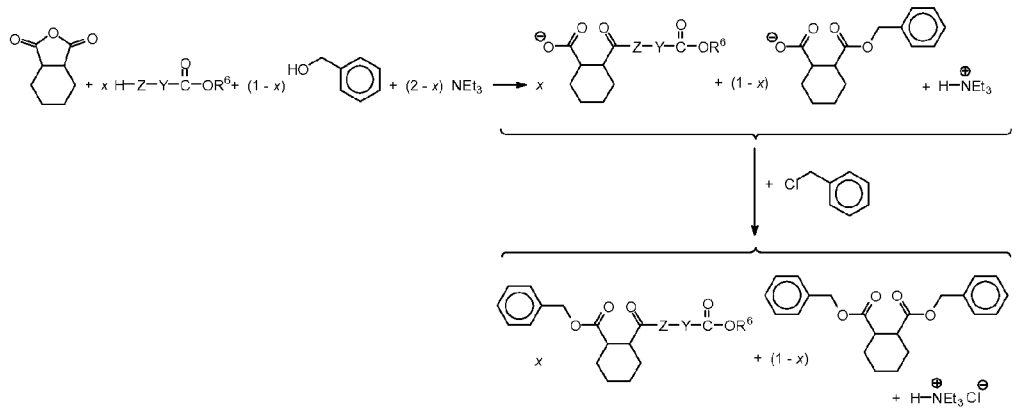
FIG. 13 shows introduction of benzyl alcohol results in dibenzyl cyclohexane-1,2-dicarboxylate.

The invention includes three strategies for making blends of dibenzyl cyclohexane-1,2-dicarboxylate with triesters of this invention:
1. Add dibenzyl cyclohexane-1,2-dicarboxylate directly.
2. Add benzyl alcohol with or in sequence with the α- or β-hydroxyesters or thioesters to the starting anhydride. See FIG. 13.
3. Add water with or in sequence with the α- or β-hydroxyesters or thioesters to the starting anhydride, and subsequently add more benzyl chloride and amine. See FIG. 12.

While advantages are found in each of these singular aspects of procedure, collectively these aspects are synergistic.

Figure 14:
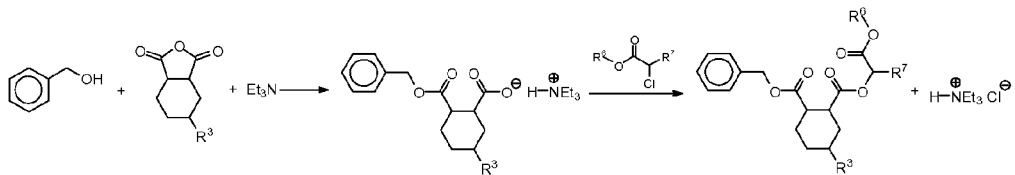
FIG. 14 alternative synthesis of glycolyl and lactyl benzyl cyclohexane-1,2-dicarboxylates.

Ethyl 2-chloroacetate [CAS No. 105-39-5] is an industrially produced compound that can be used to advantage in synthesizing benzyl ethylglycolyl cyclohexane-1,2-dicarboxylate (See FIG. 14.). Similarly methyl 2-chloroacetate [CAS No. 96-34-4] can be used to synthesize benzyl methylglycolyl cyclohexane-1,2-dicarboxylate. This route is less versatile than the route using benzyl chloride and alpha-hydroxy esters. Starting materials are less prevalent, synthesis of thioglycolate esters is not easily addressed using this scheme, and different byproducts are expected.

As described hereinabove, the present invention solves many problems associated with conventional plasticizers. However, it will be appreciated that various changes in the details, materials and formulations, which have been herein described and illustrated in order to explain the nature of the invention, may be made by those skilled in the art without departing from the principle and scope of the invention, as expressed in the appended claims.

What is claimed is:

1. A method of making a benzyl cis-cyclohexane 1,2-dicarboxylate triester comprising the steps:
  a. forming a reaction mixture by reacting the following three components:
    i. a synthetic or biobased reagent selected from the group consisting of an alpha-hydroxyester and a beta-hydroxyester,
    ii. an anhydride selected from the group consisting of cis-hexahydrophthalic anhydride, 4-methylcyclohexane-1,2-dicarboxylic anhydride, and 3-methylcyclohexane-1,2-dicarboxylic anhydride, and
    iii. an alkylamine catalyst; and
  b. contacting benzyl chloride with the reaction mixture to yield a product that is free of phthalates and includes at least one benzyl cis-cyclohexane 1,2-dicarboxylate trimester;
  wherein the benzyl cis-cyclohexane 1,2-dicarboxylate triester has the structure:

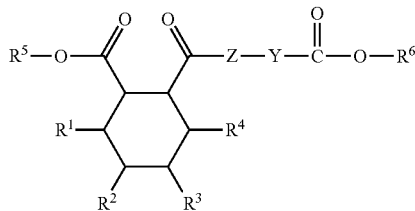

wherein $R^1$ and $R^4$ are independently selected from the group consisting of H, $CH_3$, bridging O, bridging $CH_2$, and bridging $CH_2$—$CH_2$, with each bridging unit defining coincident $R^1$ and $R^4$ groups;
  wherein $R^2$ and $R^3$ are independently selected from the group consisting of H, $CH_3$, and C-C30 linear or branched, cyclic or acyclic, substituted or unsubstituted hydrocarbyl groups;
  wherein $R^5$ is selected from the group consisting of benzyl and substituted benzyl groups;
  wherein $R^6$ is a C1-C12 linear or branched, substituted or unsubstituted, aryl or aliphatic hydrocarbyl group;
  wherein Z is O or S;
  wherein Y is selected from the group consisting of $CH_2$, $CH(R^7)$, $C(CH_3)_2$, $CH_2$—$CH_2$, $CH(R^7)$—$CH_2$, and $CH_2$—$C(=CH_2)$; and
  wherein $R^7$ is selected from the group consisting of H and a C1-C12 linear or branched, substituted or unsubstituted, aryl or aliphatic hydrocarbyl group.

2. The method of claim 1, wherein the synthetic or biobased reagent is a hydroxyester selected from the group consisting of alpha-hydroxyesters, lactate esters, mandelic acid esters, and glycolate esters.

3. The method of claim 1, wherein the synthetic or biobased reagent is a C4-C12 alpha-hydroxyester.

4. The method of claim 1, wherein the synthetic or biobased reagent is a glycolate ester selected from the group consisting of butyl glycolate, ethyl glycolate, methyl glycolate and combinations thereof.

5. The method of claim 1, wherein the synthetic or biobased reagent is a beta-hydroxyester selected from hydroxypropionate esters and C4-C12 beta-hydroxyesters.

6. The method of claim 1, wherein the alkylamine catalyst is selected from the group consisting of alkyl-pyridines, alkyl-pyramidines, alkyl-piperidines, trimethyl amine, triethyl amine, N-methylpiperidine and combinations thereof.

7. The method of claim 1, wherein the at least one benzyl cis-cyclohexane 1,2-dicarboxylate triester is selected from the group consisting of (methyl 2-carboxyethyl) cyclohexane-1,2-dicarboxylate triester, (ethyl 2-carboxyethyl) cyclohexane-1,2-dicarboxylate triester, (propyl 2-carboxyethyl) cyclohexane-1,2-dicarboxylate triester, (butyl 2-carboxyethyl) cyclohexane-1,2-dicarboxylate triester, (2-ethylhexyl 2-carboxyethyl) cyclohexane-1,2-dicarboxylate triester and combinations thereof.

8. The method of claim 1, wherein the at least one benzyl cis-cyclohexane 1,2-dicarboxylate triester is selected from the group consisting of (methyl lactyl) benzyl cyclohexane-1,2-dicarboxylate triester, (ethyl lactyl) benzyl cyclohexane-1,2-dicarboxylate triester, (propyl lactyl) benzyl cyclohexane-1,2-dicarboxylate triester, (butyl lactyl) benzyl cyclohexane-1,2-dicarboxylate triester, (2-ethylhexyl lactyl) benzyl cyclohexane-1,2-dicarboxylate triester and combinations thereof.

9. The method of claim 1, wherein the at least one benzyl cis-cyclohexane 1,2-dicarboxylate triester is selected from the group consisting of (methyl carboxymethyl) benzyl cyclohexane-1,2-dicarboxylate triester, (ethyl carboxymethyl) benzyl cyclohexane-1,2-dicarboxylate triester, (propyl carboxymethyl) benzyl cyclohexane-1,2-dicarboxylate triester, (butyl carboxymethyl) benzyl cyclohexane-1,2-dicarboxylate triester, (2-ethylhexyl carboxymethyl) benzyl cyclohexane-1,2-dicarboxylate triester and combinations thereof.

10. A plastisol including a thermoplastic polymer and the benzyl cis-cyclohexane-1,2-dicarboxylate triester made by the method of claim 1.

11. The method of claim 5, wherein the synthetic or biobased reagent is (butyl 1-methyl-2-carboxyethyl) benzyl cyclohexane-1,2-dicarboxylate.

12. The plastisol of claim 10, wherein the thermoplastic polymer is halogenated.

13. The halogenated plastisol of claim 11, wherein the halogenated thermoplastic polymer is selected from the group consisting of vinyl halide resin, polyvinyl chloride, copolymers of polyvinyl chloride, chlorinated polyethylene, chlorosulfonated polyethylene, chlorinated polyvinyl chloride, vinylidene chloride polymers, vinyl chloride-vinyl ester copolymers, vinyl chloride-vinyl ether copolymers, vinyl chloride-vinylidene copolymers, vinyl chloride-propylene copolymers, chlorinated polyethylene, polyvinyl bromide, polyvinyl fluoride, copolymers thereof and combinations thereof.

14. A method of plasticizing a plastic composition comprising the step:
  combining the following two components:
    a. a benzyl cis-cyclohexane-1,2-dicarboxylate triester made by the method of claim 1, and
    b. a plastic composition.

15. A method of making a benzyl 2-[(alkoxycarbonylmethylthio)carbonyl] cyclohexanecarboxylate comprising the steps:
   a. forming a reaction mixture by reacting the following three components:
      i. a thioglycolic acid ester,
      ii. a cis-hexahydrophthalic anhydride, and
      iii. an alkylamine catalyst; and
   b. adding benzyl chloride to the reaction mixture to form at least one benzyl 2-[(alkoxycarbonylmethylthio)carbonyl] cyclohexanecarboxylate;
   wherein the benzyl 2-[(alkoxycarbonylmethylthio)carbonyl] cyclohexanecarboxylate has the structure:

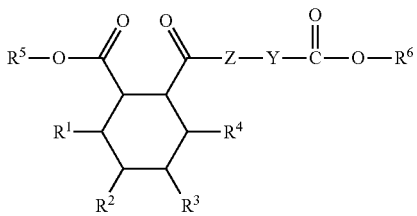

wherein $R^1$ and $R^4$ are independently selected from the group consisting of H, $CH_3$, bridging O, bridging $CH_2$, and bridging $CH_2$—$CH_2$, with each bridging unit defining coincident $R^1$ and $R^4$ groups;
   wherein $R^2$ and $R^3$ are independently selected from the group consisting of H, $CH_3$, and C-C30 linear or branched, cyclic or acyclic, substituted or unsubstituted hydrocarbyl groups;
   wherein $R^5$ is selected from the group consisting of benzyl and substituted benzyl groups;
   wherein $R^6$ is a C1-C12 linear or branched, substituted or unsubstituted, aryl or aliphatic hydrocarbyl group;
   wherein Z is S;
   wherein Y is selected from the group consisting of $CH_2$, $CH(R^7)$, $C(CH_3)_2$, $CH_2$—$CH_2$, $CH(R^7)$—$CH_2$, and $CH_2$—$C(=CH_2)$; and
   wherein $R^7$ is selected from the group consisting of H and a C1-C12 linear or branched, substituted or unsubstituted, aryl or aliphatic hydrocarbyl group.

16. A composition comprising:
   a benzyl cis-cyclohexane-1,2-dicarboxylate triester having the structure:

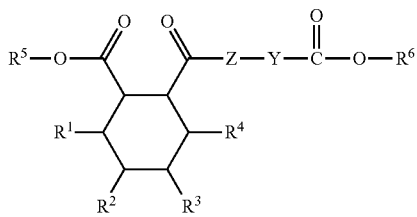

wherein $R^1$ and $R^4$ are independently selected from the group consisting of H, $CH_3$, bridging O, bridging $CH_2$, and bridging $CH_2$—$CH_2$, with each bridging unit defining coincident $R^1$ and $R^4$ groups;
   wherein $R^2$ and $R^3$ are independently selected from the group consisting of H, $CH_3$, and C1-C30 linear or branched, cyclic or acyclic, substituted or unsubstituted hydrocarbyl groups;
   wherein $R^5$ is selected from the group consisting of benzyl and substituted benzyl groups;
   wherein $R^6$ is a C1-C12 linear or branched, substituted or unsubstituted, aryl or aliphatic hydrocarbyl group;
   wherein Z is O or S;
   wherein Y is selected from the group consisting of $CH_2$, $CH(R^7)$, $C(CH_3)_2$, $CH_2$—$CH_2$, $CH(R^7)$—$CH_2$, and $CH_2$—$C(=CH_2)$; and
   wherein $R^7$ is selected from the group consisting of H and a C1-C12 linear or branched, substituted or unsubstituted, aryl or aliphatic hydrocarbyl group.

17. The composition of claim 16, wherein the benzyl cis-cyclohexane-1,2-dicarboxylate triester is selected from the group consisting of (butyl carboxymethyl) benzyl cyclohexane-1,2-dicarboxylate triester; (ethyl lactyl) benzyl cyclohexane-1,2-dicarboxylate triester; (butyl lactyl) benzyl cyclohexane-1,2-dicarboxylate triester; and (butyl 1-methyl-2-carboxyethyl) benzyl cyclohexane-1,2-dicarboxylate triester.

* * * * *